United States Patent
Uemura et al.

(10) Patent No.: US 6,306,382 B1
(45) Date of Patent: *Oct. 23, 2001

(54) KERATOTIC PLUG REMOVER

(75) Inventors: Tomohiro Uemura, Chiba; Masanori Tanahashi, Funabashi; Yoshinao Kono, Wakayama, all of (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/748,549

(22) Filed: Nov. 12, 1996

Related U.S. Application Data

(60) Division of application No. 08/463,274, filed on Jun. 5, 1995, now abandoned, which is a continuation-in-part of application No. 08/210,778, filed on Mar. 21, 1994, now Pat. No. 5,512,277, which is a continuation-in-part of application No. 07/882,979, filed on May 14, 1992, now abandoned.

(30) Foreign Application Priority Data

| May 15, 1991 | (JP) | 3-110342 |
| Feb. 12, 1992 | (JP) | 4-025354 |
| Apr. 8, 1992 | (JP) | 4-087032 |
| Apr. 8, 1992 | (JP) | 4-087033 |

(51) Int. Cl.⁷ ............. A61K 31/74; A61K 7/48
(52) U.S. Cl. .......... 424/78.03; 424/402
(58) Field of Search ........... 424/78.08, 78.03, 424/402, 780.04, 78.05

(56) References Cited

U.S. PATENT DOCUMENTS

| D. 351,924 | 10/1994 | Glover . |
| 3,428,043 | 2/1969 | Sheperd . |
| 4,010,254 | 3/1977 | Koulbanis et al. . |
| 4,126,142 | 11/1978 | Saute . |
| 4,377,160 | 3/1983 | Romaine . |
| 4,471,871 | 9/1984 | Rockliffe et al. . |
| 4,585,797 | 4/1986 | Cioca . |
| 4,752,472 | 6/1988 | Kligman . |
| 4,762,124 | 8/1988 | Kerch et al. . |
| 4,942,029 * | 7/1990 | Scheps ............ 424/78 |
| 4,948,585 * | 8/1990 | Schlein ........... 424/402 |
| 4,990,339 | 2/1991 | Scholl et al. . |
| 5,026,552 * | 6/1991 | Gueret et al. ............ 424/401 |
| 5,254,338 | 10/1993 | Sakai et al. . |
| 5,344,655 * | 9/1994 | Sakai et al. ............ 424/78.27 |
| 5,466,546 | 11/1995 | Glover . |
| 5,512,277 * | 4/1996 | Uemura et al. ............ 424/78.03 |
| 5,567,787 * | 10/1996 | Kwak et al. ............ 526/271 |
| 5,605,694 | 2/1997 | Nadaud et al. . |
| 5,723,138 | 3/1998 | Bae et al. . |
| 5,736,128 | 4/1998 | Chaudhuri et al. . |
| 5,744,147 * | 4/1998 | Cauwet et al. ............ 424/401 |
| 5,811,107 * | 9/1998 | Gangadharan et al. ............ 424/401 |
| 5,935,596 * | 8/1999 | Crotty et al. ............ 424/448 |
| 5,968,537 | 10/1999 | Crotty et al. . |
| 5,985,300 | 11/1999 | Crotty et al. . |
| 5,993,838 | 11/1999 | Crotty et al. . |

FOREIGN PATENT DOCUMENTS

| 206114 | 11/1959 | (AT) . |
| 0 045 493 | 2/1982 | (EP) . |
| 0 063 875 | 3/1982 | (EP) . |
| 331528 A1 | 9/1989 | (EP) . |
| 446636A2 | 9/1991 | (EP) . |
| 0 514 760 B1 | 11/1992 | (EP) . |
| 0826 364 A2 | 3/1998 | (EP) . |
| 0 323 652 | 7/1998 | (EP) . |
| A-934734 A1 | 8/1999 | (EP) . |
| 965332A2 | 12/1999 | (EP) . |
| 2107186 * | 4/1983 | (GB) ............ 424/78.03 |
| 2 144 133 * | 2/1985 | (GB) . |
| 46-35760 | 10/1971 | (JP) . |
| 477560 * | 3/1972 | (JP) ............ 424/78.03 |
| 49-132247 | 12/1974 | (JP) . |
| 5327344 * | 8/1978 | (JP) ............ 424/78.03 |

(List continued on next page.)

OTHER PUBLICATIONS

"Les Masques De Beaute" A. Julien et al Parfums, Cosmetiques, Aromes Dec. 1986.*

Opposition by Unilever plc, KAO Corporation, European Patent No. 0 826 364 B, European Patent Application No. 97100138.3.

Information Offer Form, Mar. 7, 2000 w/English Translation.

Fragrance Science and its English Translation.

Fragrance Jornal Aug. 2000, (w/translation) *Develpment of the Product and Its Sale in Japan* P92–1487 (Japanese Laid–Open Hei 11–217312) (Translations).

Journal of Detmatological Treatment (1999) 10, 47–52, pp. 47–51, A Pagnoni et al.

Parfume, Cosmetiques, Aromes No. 72—Dec. 1986, *Cosmetologie Les masques de beaute* (*Premiere partie*) pp. 61–64, with 13p. English Translation.

Abstract, 1p. JP2–258713.
Abstract, 1p. JP57–134415.
Abstract, 1p. JP 61–275212.
Abstract, 2pp. JP 61–22012.

(List continued on next page.)

*Primary Examiner*—Peter F. Kulkosky
(74) *Attorney, Agent, or Firm*—Oblon, Spivak, McClelland, Maier & Neustadt, P.C.

(57) ABSTRACT

A keratotic plug remover composition comprising a polymer compound having a salt forming group is disclosed. The composition according to the invention can effectively remove keratotic plugs in the skin pores, so that the conspicuousness of the skin pores is mitigated and clean and healthy skin pores can be maintained. The composition does not hurt the skin.

7 Claims, No Drawings

FOREIGN PATENT DOCUMENTS

| | | |
|---|---|---|
| 54-49334 | 4/1979 | (JP) . |
| 54-56682 | 4/1979 | (JP) . |
| 55-127312 | 10/1980 | (JP) . |
| 56-97207 | 8/1981 | (JP) . |
| 56-131511 | 10/1981 | (JP) . |
| 57-56408 | 4/1982 | (JP) . |
| 57-77611 | 5/1982 | (JP) . |
| 57 134415 | 8/1982 | (JP) . |
| 58-18048 | 10/1983 | (JP) . |
| 58 216109 | 12/1983 | (JP) . |
| 59-93012 | 5/1984 | (JP) . |
| 60-165902 | 8/1985 | (JP) . |
| B-60-45522 | 10/1985 | (JP) . |
| 61-15813 | 1/1986 | (JP) . |
| 61-212325 | 9/1986 | (JP) . |
| 61-26007 | 11/1986 | (JP) . |
| 62-93210 | 4/1987 | (JP) . |
| A-62-93210 | 4/1987 | (JP) . |
| A-62-127393 | 6/1987 | (JP) . |
| 63-35511 | 2/1988 | (JP) . |
| 63-57508 | 3/1988 | (JP) . |
| 63-57509 | 3/1988 | (JP) . |
| A-63-88120 | 4/1988 | (JP) . |
| 2-145505 | 6/1990 | (JP) . |
| 2-258713 | 10/1990 | (JP) . |
| 2-270811A2 | 11/1990 | (JP) . |
| 5-221843 | 8/1993 | (JP) . |
| 7-330575 | 12/1995 | (JP) . |
| 3033044 | 10/1996 | (JP) . |
| A-319213 | 12/1996 | (JP) . |
| 10-317-439 | 8/1999 | (JP) . |
| WO 90/02774 | 3/1990 | (WO) . |
| WO 93/05893 | 4/1993 | (WO) . |
| WO 99/38473 | 8/1999 | (WO) . |
| WO 99/45891A1 | 9/1999 | (WO) . |

OTHER PUBLICATIONS

Abstract, 2pp. JP60–208909.
Abstract, 1p. JP60–258114.
Abstract, 1p. JP58–167510.
*Design Gazette,* Japanese Publication, Jun. 22, 1988, 1p.
Paper presented by Inventor, Mr. Tomohiro Uemura, at "Surface Chemistry" Convention, Kansai of Japan, Oct. 30, 1998, Title page w. pp 30–40.
Paper presented by Mr. Suzuki, in *Chemcial and Industry,* Bi–Monthly Publication, 1998 Issue, pp. 868–870.
English Translation of P92–183JP Office Action.
English Translation of P92–183JP Response.
Englsih Translation of P92–183JP Amendment.
English Translation of P92–183JP Notice of Allowance.
English Translation of P92–183JP Amendment of Claim.
Prosecution History of P92–183 EP (See EP 0 514 760 B1).
Prosecution Histroy of P92–183 EP (Div) 9pp. European Patent Application No. 97 100 138.3, w. Copy of EP 0 826 364 A3.
"The Science of Fragrances and Cosmetics" (3p. English Translation of Japanese Publication–Attached).
Englsih Translation (1 paragraph) of "Carboxyvinlpolymer" w. Japanese Publication (2pp.).
Japanese Reference 36–550 (2pp.).
Japanese Reference 4–087032, 1975, (4pp.).
Englsih Translation of Japanese Priority Document (Feb. 12, 1992)#1, w. Copy of Japanese Document of P92–183(US), Laid Open (Kokai) No. 221843/1993, pp. 47–51, in Opposition to P91–1390.
English Translation of (Feb. 12, 1992), Japanese Priority Document #2, w. Copy of Japanese Document of P92–183(US) Laid Open (Kokai) No. 221843/1993, pp. 42–46, in Opposition to P91–1390.
Englsih Translation of (Apr. 8, 1992) Japanese Priority Document of P92–183(US), Laid–Open (Kokai) No. 221843/1993, pp 33–40, in Opposition to P92–150.
*Die Angewandte Makromolekulare Chemie* 181 (1990) 93–101.
Notice of Opposition, Jun. 23, 2000 (w. Translation and cited documents) P92–183Jp Opposition (1).
P92–183 JP Opposition (2).
P92–183 JP Opposition (3).
Paper by Mr. Koichi Ishida's and translation (pp. 326–334), Chapter 6—*Technique for Preparation of Pack in a Form of Sheet.*
Paper by Mr. Koichi Ishida's and translation (pp. 114–118) *Development of "Biore Cleansing Pack for Pores".*
Abstract, 1p. JP–A–63–88120 (Counterpart of U,S, Patent 4,942,029 Above).*

\* cited by examiner

KERATOTIC PLUG REMOVER

This is a Continuation of application Ser. No. 08/463,274, filed on Jun. 5, 1995, now abandoned, which is a Continuation of application Ser. No. 08/210,778 filed on Mar. 21, 1994, now U.S. Pat. No. 5,512,277, issued Apr. 30 1996, which was a Continuation of application Ser. No. 07/882,979, filed on May 14, 1992, now abandoned.

BACKGROUND OF THE INVENTION

1. Field of the Invention

The present invention relates to a keratotic plug remover which excellently removes keratotic plugs formed in the pores of the skin, and a method of removing keratotic plugs from the skin utilizing such a keratotic plug remover.

2. Discussion of the Background

Having conspicuous pores in the skin is a serious skin problem, especially for women, and is mainly caused by keratotic plugs formed in the pores of the skin. Keratotic plugs are dead epidermal cells keratinized together with sebaceous matters and dirt which plug the pores of the skin. If proper treatment is not given, not only conspicuous pores but also various skin troubles result. Accordingly, removal of keratotic plugs is advisable in view of the health and beauty of the skin.

Ordinary face detergents, make-up removers, however, cannot sufficiently remove the keratotic plugs.

Pack preparations, which are applied to the skin and peeled off after dried, and which generally contain a non-ionic polymer such as polyvinyl alcohol and polyvinyl pyrrolidone as a major component of a film forming agent, are still not sufficiently effective for removing dirt from the skin pores and especially for removing keratotic plugs.

Thus, there remains a need for a keratotic plug remover which can effectively remove keratotic plugs formed in the pores of the skin and a method of removing keratotic plugs from the skin utilizing such plug removers.

SUMMARY OF THE INVENTION

Accordingly, it is one object of the present invention to provide novel keratotic plug removers which effectively remove keratotic plugs from the skin.

It is another object of the present invention to provide a method for removing keratotic plugs from the skin which utilized such keratotic plug removers.

These and other objects which will become apparent during the following detailed description have been achieved by the inventors discovery that a keratotic plug remover which comprises a synthetic polymer having a salt forming group can effectively remove keratotic plugs and dirt from the pores of the skin.

DETAILED DESCRIPTION OF THE PREFERRED EMBODIMENTS

The salt forming group of the polymer which is useful in the present invention is not particularly limited as long as it can form a salt in the presence of an acid or a base, and anionic, cationic and anphoteric groups are suitable. Examples of the salt forming group are carboxyl, sulfonic acid group, sulfuric acid residual group ($-OSO_3H$), phosphoric acid residual group ($-OPO_3H_2$), nitric acid residual group ($-NO_2$), amino group, ammonium group, and the like. Two or more of these groups may be present in one compound.

The polymer compound which is useful in the present invention is preferably water-soluble from the viewpoint of good appearance, but it is not necessarily water-soluble for the purpose of achieving the effects of this invention. The compounds which are not water-soluble may take the form of dispersion and/or emulsion.

Examples of the polymers useful in the present invention include: hyaluronic acid, sodium hyaluronate, sodium chondroitin sulfate which are mucopolysaccharides; alginic acid, sodium alginate, ammonium alginate, sodium carboxylmethylcellulose, and carboxymethyl amylose which are hemicelluloses. These are of natural origin or semi-synthesized polymers. In this invention, synthesized polymers are more preferable. Examples of the synthesized polymers include (A) polymers of one or more monomers listed in (1) to (3) below, (B) copolymers of the monomers as listed in (1) to (3) and another monomer which has no salt forming group, such as vinyl esters of aliphatic carboxylic acid such as vinyl acetate, (meth)acrylic esters such as methyl methacrylate, alkyl vinyl ethers such as methyl vinyl ether, N-vinyl cyclic amides such as N-vinylpyrrolidone, styrene and alkyl- substituted styrene, and (c) mixtures of the above-mentioned polymers.

(1) Anionic monomers

Acrylic acid (AA), Methacrylic acid (MA), Maleic acid, itaconic acid and the like, which are unsaturated carboxylic acid monomers or their anhydrides or their salts;

Styrene sulfonic acid, 2-Acrylamide-2-methyl propane sulfonic acid (AMS) and the like, which are unsaturated sulfonic acid monomers or their salts;

Vinylphosphonic acid, Acid phosphoxyethyl (meth)acrylate and the like, which are unsaturated phosphoric monomers.

(2) Cationic monomers

Dimethylaminoethyl acrylate (DAEA), Dimethylaminoethyl methacrylate (DMAEMA), Dimethylaminopropylacrylamide (DMAPAAm), Dimethylaminopropyl methacrylamide (DMAPMAAm), and the like, which are (meth)acrylamides or (meth)acrylic acid esters having a dialkylamino group;

Dimethylaminostyrene (DMASt), Dimethyaminomethyl-styrene (DMAMSt) and the like, which are styrenes having a dialkylamino group;

4-Vinyl pyridine, 2-vinyl pyridine and the like, which are vinyl pyridines;

Quaternarized products of these with a known quatenarizing agent such as alkyl halide, benzyl halide, alkyl or aryl sulfonic acid, or dialkyl sulfate.

(3) Amphoteric monomers

N-(3-sulfopropyl)-N-acryloyloxyethyl-N,N-dimethylammonium betaine, N-(3-sulfoproyl-)-N-methacroylamidepropyl-N,N-dimethylammoniuz betaine, N-(3-carboxymethyl)-N-methacroylamidepropyl-N,N-dimethylammonium betaine, N-carboxymethyl-N-methacroyloxyethyl-N, N-dimethylammonium betaine.

When the salt forming group of these polymers is not ionized, it is preferred to ionize it via neutralization with known acids such as hydrochloric acid and sulfuric acid which are inorganic acids; acetic acid, propionic acid, lactic acid, succinic acid, glycol acid which are organic acids, or with known bases such as triethylamine, trimethylamine which are tertiary amines; ammonia; or sodium hydroxide.

Among the mentioned polymer compounds, preferred ones in view of the mildness to the skin and high effectiveness for removing keratotic plugs are polymers of one or more cationic monomers, copolymers between one of these polymers and an amphoteric monomer or a monomer having no salt forming groups, and mixtures of these polymers.

Preferable examples of the cationic monomers include dimethylaminoethylacrylate (DMAEA), dimethylaminoethylmethacrylate (DMAEMA), dimethylaminopropylacrylamide (DMAPAAm), dimethylaminopropyl methacrylamide (DMAPMAAm) and the like, which are (meth)acrylic esters or (meth)acrylamides having a dialkylamino group; and quaternary compound of them which are quaternarized with a known quaternarizing agent such as alkyl halide, benzyl halide, alkyl or aryl sulfonic acid or dialkyl sulfate. Among them, especially preferred are dipethylaminoethylmethacrylate (DMAEMA) and its quaternarized products; quaternarized products of dimethylaminopropyl methacrylamide (DMAPAAm); polymers of one or more of these monomers; copolymers between one or more of these monomers and the above-mentioned monomers; and mixtures thereof.

The molecular weight (weight average) of these polymers is preferably in the range of from 10,000 to 1,500,000, and especially from 100,000 to 1,000,000. Molecular weights less than 10,000 will result in insufficient film strength and easily breakable films upon peeling-off. Polymers having a molecular weight over 1,500,000 are difficult to manufacture.

The preferable amount of the polymer to be incorporated linto the keratotic plug remover preparation according to the invention is from 0.01 to 70% by weight, preferably 5 to 40% by weight based on the total weight of the preparation.

The above-mentioned synthesized polymers are used as dissolved in a solvent. The solvent useful n this invention is volatile and is not particularly limited as long as it can stably dissolve the polymers and is safe to the skin. Examples of such solvents include water, ethanol, isopropyl alcohol (IPA) and the like. They are used singly or in combination. The amount of the solvent is modified depending on the properties of the polymer compounds, optional ingredients and forms of the preparation, and is generally from 30 to 99.99% by weight, and preferably from 60 to 95% by weight, based on the total weight of the composition.

The efficacy of the keratotic plug remover of this invention is enhanced when a pigment is further incorporated together with the mentioned polymers. The pigment is not particularly limited, and both organic and inorganic pigments can be used. Examples of the inorganic pigments are zinc oxide, titanium oxide, silica, alumina, barium sulfate, zirconium oxide, calcium carbonate, calcium silicate, ceramics, hydroxzypatite, boron nitride, sericite, mica, talc, kaolin, montmorillonite, hectorite, saponite, black iron oxide, yellow iron oxide, red iron oxide, prussian blue, ultramarine, carbon black, pearlescent pigments and so on. Examples of the organic pigments are silk powders, cellulose powders, poly(meth)acrylic ester resins, polyamide resins, polyolefin resins, polyimide resins, polyurethane resins, polyester resins, polyether resins, polyvinyl chloride resins, urea resins, polyformaldehyde resins, polycarbonate resins, polyvinylacetate resins, polyvinylidane chloride resins, polyacrylonitrile resins, polysulfone resins, polystyrene resins, polyurea resins, silicone resins, melamine resins, polytetrafluoroethylene resins, rake pigments and azo dyes.

The particle size of the pigments is from 0.001 to 1000 micrometers, and preferably from 0.01 to 500 micrometers. Particle size of less than 0.001 micrometer is not preferred because good dispersibility cannot be obtained. Particle size over 1000 micrometers is not preferred, either, because of an unfavorable sensation to the skin. The mentioned pigments can be used as a complex or a mixture of one or more, if desired. The amount of the pigment is from 0.1 to 70% by weight, preferably from 1 to 40% by weight based on the total weight of the preparation.

When an oil component is further incorporated together with the polymers, the keratotic plug remover of this invention can achieve excellent removal of keratotic plugs without giving irritation to the skin. This is because the strength of the film at which it breaks upon peeling-off can be controlled by the oil component.

The oil component which is useful in this invention is a glycerol derivative represented by formula (I):

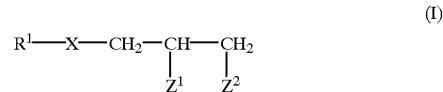

(I)

wherein one of $Z^1$ and $Z^2$ represents $R^2$-y- and the other represents a hydroxyl group or $R^3$-y-, and $R^1$, $R^2$ and $R^3$ independently represent a hydrocarbon group, the total carbon number of which ranges from 13 to 40, and the hydrocarbon group may or may not be substituted by a silicone residual group, X and Y independently represent an oxygen atom or a group —COO—, (a carboxyl group in thih the C atom is bonded to $R^1$, $R^2$ or $R^3$). Other oily ingredients which are generally incorporated into cosmetic preparations can also be used. Examples of the oil component which is useful in this invention include vegetable oils such as avocado oil, tsubaki oil, macadamia nut oil, olive oil and jojoba oil; animal oils and fats such as beef tallow, lard and egg yolk fat; aliphatic acids such as oleic acid and isostearic acid; alcohols such as hexadecyl alcohol and oleyl alcohol ; esters such as cetyl 2-ethylbexanoate, 2-ethylhexyl palmitate, 2-octyldodecyl myristate, neopentyl glycol di-2-ethyl hezanoate, 2-octyldodecyl oleate, isonropyl myristate, glycerol triisostearate, mono-2-ethylhexanoic glyceryl di-paramethoyycinnamate; and hydrocarbons such as dimethylpolysiloxane, dimethyl cyclopolysiloxane, methylphenyl polysiloxane, methylhydrogen polysiloxane, octamethyl cyclotetrasiloxane, octamethyl cyclopentasiloxane, decamethylcyclopentasiloxane, liquid paraffin, squalane, vaseline and solid paraffin.

Among these oil components, glycerol derivatives of formula (1) which are liquid at 20° C. are preferred, and particularly, tri-2-ethylhexanoic glycerol, 1-isostearoyl-3-myristoyl glycerol, 2-ethylhexanoic diglyceride, 1-hexyl-3-undecamethylhexasiloxy propynyl glycerol are most preferred.

The amount of the oil components to be incorporated into the keratotic plug remover of this invention is from 0.5 to 30% by weight, preferably, 1 to 15% by weight based on the total weight of composition.

The keratotic plug remover preparation of this invention can further contain optional ingredients which are generally incorporated into cosmetic preparations. Examples of such optional ingredients include ethylene glycol, diethylene glycol, triethylene glycol and higher polyethylene glycols; propylene glycol, dipropylene glycol and higher polypropylene glycols, 1,3-butylene glycol, 1, 4-butylene glycol and other butylene glycols; glycerol, diglycerol and higher polyglycerols;.sugaralcohols such as sorbitol, mannitol, xylitol and maltitol; ethylene oxides (hereinafter referred to as EO) such as glycerols; addition products of propylene oxide (hereinafter referred to as PO); EO or PO adducts of sugaralcohols; monosaccharides such as galactose, glucose and fructose, and their EO or PO adducts; polysaccharides such as maltose and lactose, and their EO or PO adducts (polyols); surfactants such as POE alkyl ethers (POE is polyoxyethylene), POE branched alkyl ethers, POE sorbitan esters, POE glycerol fatty acid esters, POE hydrogenated castor oil, sorbitan ester, glycerol fatty acid esters and polyglycerol fatty acid ester; drugs such as vitamins, antiphlogistics, activators, UV absorbers and the like; water-swelling clay minerals such as montorillonite, saponite and hectorite; polysaccharides such as carageenan, xanthangum, sodium alginate, pullulan, methylcellulose, carboxymethylcellulose, hydroxyethylcellulose and hydroxypropylcellulose; synthetic polymers such as carboxyvinyl polymers, polyvinyl pyrrolidones and polyvinyl alcohols. They are incorporated into the preparation of the present invention in such amounts that will not impede the effects of the invention. In particular, when polyols are used, they are preferably incorporated by 0.01 to 50% by weight based on the total preparation.

The keratotic plug remover according to this invention may take a form of a poultice using cotton cloth, rayon cloth, tetron cloth, nylon cloth, either woven or non-woven, or using a plastic film sheet, beside pack preparations.

The keratotic plug remover of this invention can be manufactured according to conventional processes for the manufacture of ordinary packs and poultice.

The manner of removing keratotic plugs by the use of the keratotic plug remover of the invention is the same as the manner of using ordinary packs and poultice. Namely, when a pack preparation is used, it is first applied to the part of the skin which has keratotic plugs, particularly likely to the nose, chin and forehead, and after dried, it is peeled off.

Since the keratotic plug remover of this invention effectively removes keratotic plugs, the conspicuousness of the skin pores is mitigated, skin pores are maintained clean, and healthy skin can be obtained. Further, the remover of this invention does not hurt the skin.

Other features of the invention will become apparent in the course of the following descriptions of exemplary embodiments which are given for illustration of the invention and are not intended to be limiting thereof.

EXAMPLES

Where not otherwise indicated all amounts in the examples are in terms of % by weight based on the total weight of the composition.

Example 1

Keratotic plug removers were prepared according to the pack preparation method mentioned below using the polymers listed in Table 1. A panel washed their face and used the preparation on their faces at an application rate of 0.1 ml/cm$^2$. The conditions of use were a temperature of 25° C., 50% humidity for 30 minutes. When 30 minutes had passed, the pack was peeled off. The ratio of removal of the keratotic plugs was calculated according to the following equation for evaluation.

$$\text{Removal ratio of keratotic plugs} = \frac{\text{number of keratotic plugs adhered on 1 cm}^2 \text{ pack}}{\text{number of keratotic plugs existing in the 1 cm}^2 \text{ wing skin of nose}} \times 100$$

The results are also shown in. Table 1.

Evaluation:

A: over 20% removal ratio of keratotic plugs

B: 5 to 20% removal ratio of keratotic plugs

C: less than 5% removal ratio of keratotic plugs

Preparation:.

| Polymer | 15 to 20% by weight |
| --- | --- |
| Glycerol | 5 |
| HCO60 (polyoxyethylene hydrogenated castor oil 60EO adduct) | 1 |
| Ethanol | 5 |
| Perfume | 0.5 |
| Antiseptic | suitable amount |
| Purified water | 67.5 to 72.5 |
| Total | 100.0 |

TABLE 1

| | Polymers | Anionic/Cationic | Evaluation (Removal of keratotic plugs) |
| --- | --- | --- | --- |
| IONIC | Poly 2-acrylamide-2-methylpropane sulfonate (AMPS) (MW: 500,000) | anionic | A |
| | Polymethacroyloxymethyl succinate (MW: 200,000) | anionic | A |
| | Polymer of Na.styrene sulfonic acid (NaSS) (MW: 100,000) | anionic | A |
| | Polymer of methacrylic acid (MAA) (MW: 200,000) | anionic | A |
| | Copolymer of NaSS/MAA (1:1) (MW: 400,000) | anionic | A |
| | Polymethacroyloxyethyl trimethyl ammonium chloride (QDM) (MW: 400,000) | cationic | A |
| | Polymethacroyloxyethyl triethyl ammonium diethyl sulfate (DEAMA-DES) (MW: 300,000) | cationic | A |
| | Polymethacrylamidepropyl trimethyl ammonium | cationic | A |

TABLE 1-continued

| Polymers | | Anionic/ Cationic | Evaluation (Removal of keratotic plugs) |
|---|---|---|---|
| | chloride (NAPTAC, MW: 300,000) / polyacrylamidepropyl trimethyl ammonium chloride (DMAPAAm-Q, MW: 300,000) copolymer (8:2 by molar ratio) | | |
| NONIONIC | Polyvinyl alcohol (PVA) (MW: 100,000) | — | C |
| | Polyethylene oxide (PEO) (MW: 1,000,000) | — | C |
| | Pullulan (MW: 70,000) | — | C |
| | Hydroxyethylcellulose (HEC) (MW: 100,000) | — | C |
| | Polyvinyl pyrrolidone (PVP) (MW: 600,000) | — | C |

Example 2

Keratotic plug removers were prepared using the polymers listed in Table 2, and the removal ratio of keratotic plugs and the pain at the time of peeling-off were checked.

The polymers were individually prepared into an aqueous 20–30% by weight solution, and members of the panel used in the same manner as in Example 1.

Removal ratio of keratotic plugs:

See the equation in Example 1.

Evaluation:

(Removal ratio of keratotic plugs)

A: 35% or more

B: 20 to 34%

C: 5 to 19%

D: less than 5%

(Pain at the time of peeling-off)

slight pain: + considerable pain: ++

Example 3

Keratotic plug removers having the formulations as in Table 3 were prepared according to the conventional manner, and the keratotic plug removing performance was evaluated. The results are shown in Table 4.

Evaluation Method:

Panel members washed their faces and applied keratotic plug removers onto their checks (0.1 ml/cm$^2$). The application was allowed to set at 25° C., humidity 50% or 30 minutes, and subsequently the pack film was peeled off. The number of the members who used an invention product A on their left cheek and an invention product B on their right cheek was the same as the number of the members who used an invention product B on their left cheek and an invention product A on their right cheek.

The panel members evaluated the removers by answering "Invention product A removed better", "Invention product A and Invention product B were almost the same concerning the removal performance" or "Invention product B removed better", and their percentages were obtained.

TABLE 2

| Polymers | Anionic/ Cationic | Removal of Keratotic plugs | Pain upon peeling-off |
|---|---|---|---|
| Poly-2-acrylamide-2-methylpropane sulfonate (AMPS) (MW: 500,000) | Anionic | B | ++ |
| Polymethacryloyloxy methyl succinate (MW: 200,000) | Anionic | B | + |
| Polymer of Na.styrene sulfonic acid (NaSS) (MW: 100,000) | Anionic | A | ++ |
| Methacrylic acid (MAA) polymer (MW: 200,000) | Anionic | B | ++ |
| NaSS/MkA copolymer (1:1) (MW: 400,000) | Anionic | A | ++ |
| Polymethacryloyloxyethyl trimethylammonium chloride (QDM) (MW: 400.000) | Cationic | A | + |
| Polymethacrylamidepropyl trimethylammonium chloride (MAPTAC) (MW: 300,000) | Cationic | A | + |
| MAPTAC (MW: 300,000)/polyacrylamidepropyl trimethyl ammonium chloride (DMAPAAm-Q) (MW: 300,000) copolymer (8:2) | Cationic | A | + |
| MAPTAC (MW: 300,000)/QDM (MW: 400,000) mixture | Cationic | A | + |

TABLE 3

|  | Invention products A | | | Invention products B | |
|---|---|---|---|---|---|
| Components (% by weight) | 1 | 2 | 3 | 1 | 2 |
| Poly-2-acrylamide-2-methylpropane sulfonate (AMPS) (MW: 500,000) | 25 | 25 | — | 25 | — |
| Polymethacroyloxyethyltrimethyl ammonium chloride (QDM) (MW: 400,000) | — | — | 25 | — | 25 |
| Silica (av. particle size = 5 micrometers) | — | — | 10 | — | — |
| Zinc oxide (av. particle size: 0.04 micrometers) | 3 | — | — | — | — |
| Sericite (long axis: 5 to 10 micrometers) | — | 10 | — | — | — |
| HCO40 (Polyoxyethylene hydrogenated castor oil 60 EO adduct) | 3 | 3 | 3 | 3 | 3 |
| Glycerol | 5 | 5 | 5 | 5 | 5 |
| Perfume | 0.5 | 0.5 | 0.5 | 0.5 | 0.5 |
| Antiseptic | | | suitable amount | | |
| Purified water | | | balance | | |

TABLE 4

| Left (Right) | Right (Left) | Invention product A removed better | Invention products A and B are similar | Invention product B removed better |
|---|---|---|---|---|
| Invention product A1 | — Invention product B1 | 90 | 10 | 0 |
| Invention product A2 | — Invention product B1 | 90 | 10 | 0 |
| Invention product A3 | — Invention product B2 | 80 | 20 | 0 |

Example 4

The keratotic plug removers as formulated in Table 5 were prepared according to the conventional manner.

The obtained keratotic plug removers were used by a panel consisting of 20 members as in the same manner described in Example 1. The pain upon peeling-off was evaluated with the criteria below. The results are shown in Table 5. Concerning the keratotic plug removal, all preparations removed well.

Evaluation:

O: No pain felt
X: Pain felt

TABLE 5

|  | Invention products C | | | Invention products D | |
|---|---|---|---|---|---|
| Components (% by weight) | 1 | 2 | 3 | 1 | 2 |
| Poly-2-acrylamide-2-methylpropane sulfonate (AMPS) (MW: 500,000) | 25 | 25 | — | 25 | — |
| Polymethacroyloxy ethyl triammonium chloride (QMD) (MW: 400,000) | — | — | 25 | — | 25 |
| Tri-2-ethyl hexanoic glycerol | 3 | — | 3 | — | — |
| 2-Ethylhexanoic diglyceride | 3 | 3 | — | — | — |
| Glycerol | 5 | 5 | 5 | 5 | 5 |
| HCO40 (Polyoxyethylene hydrogenated castor oil 60 EO adduct) | 1 | 1 | 1 | 1 | 1 |
| Squalane | 1 | 1 | 1 | — | — |
| Ethanol | 5 | 5 | 5 | 5 | 5 |
| Perfume | 0.5 | 0.5 | 0.5 | 0.5 | 0.5 |
| Antiseptic | | | suitable amount | | |
| Purified water | | | balance | | |
| Pain when peeled off | O | O | O | X | X |

Example 5

The keratotic plug removers as formulated in Table 6 were prepared according to the conventional manner.

The obtained keratotic plug removers removed keratotic plugs effectively without giving pains at the time of peeling off.

TABLE 6

| Components (% by weight) | Invention products C | | | | | | | | | |
|---|---|---|---|---|---|---|---|---|---|---|
| | 4 | 5 | 6 | 7 | 8 | 9 | 10 | 11 | 12 | 13 |
| Polymethacrylamidepropyl trimethylammonium chloride (MAPTAC) (MW: 500,000) | | | | | | | | | 10 | 10 |
| Polymethacryloyloxy ethyl trimethylammonium chloride (QDM) (MW: 400,000) | | | | | | | 10 | 10 | | |
| Na.Styrene sulfonic acid / Methacrylic acid copolymer (MW: 400,000) | 25 | | | | | | | | | |
| Poly 2-acrylamide-2-methylpropane sulfonate (AMPS) (MW: 500,000) | | 30 | | | | 20 | | | | |
| Polymethacrylamide propyl trimethylammonium chloride (MAPTAC) (MW: 50,000) | | | 35 | | | | | 20 | | 20 |
| Polymethacryloyloxy ethyl trimethylammonium chloride (QDM) (MW: 70,000) | | | | 30 | 20 | | 20 | | 20 | |
| Polyvinyl alcohol (MW: 30,000) | | | | | 5 | 5 | | | | |
| PEG 200 (polyethylene glycol 200) | 5 | 5 | 5 | 5 | 3 | 3 | 3 | 3 | 3 | 3 |
| HCO 40 (Polyoxyethylene hydrogenated castor oil 40 EO adduct) | 1 | 1 | 1 | 1 | 1 | 1 | 1 | 1 | 1 | 1 |
| Squalane | 1 | 1 | 1 | 1 | | 1 | 1 | 1 | 1 | 1 |
| 2-ethylhexanoic diglyceride | 3 | | | | 2 | | 3 | 3 | 3 | 3 |
| Tri-2-ethylhexanoic glycerol | 1 | 2 | | | | | | | | |
| 1-Hexyl-3-undecamethylhexasiloxane propynyl glycerol | | | | 3 | | 2 | | 2 | | 2 |
| 1-isostearoyl-3-myristoylglycerol | | 2 | 3 | | | | 3 | | 3 | |
| Silica | | | | | 10 | | | | | |
| Sericite | | | | 10 | | | | | | |
| Perfume | 0.5 | 0.5 | 0.5 | 0.5 | 0.5 | 0.5 | 0.5 | 0.5 | 0.5 | 0.5 |
| Antiseptic | ← suitable amount → | | | | | | | | | |
| Water | ← balance → | | | | | | | | | |

Example 6

A keratotic plug remover having the following formulation was prepared.

| | |
|---|---|
| Polymethacryloyloxy trimethyl ammonium chloride (QDM) (MW: 400,000) | 27.0 wt. % |
| Sorbitol | 3.0 |
| Sericite | 3.0 |
| Ethanol | 5.0 |
| Antiseptic | suitable amount |
| Water | balance |

Example 7

A keratotic plug remover having the following formulation was prepared.

| | |
|---|---|
| Polymethacryloyloxy trimethyl ammonium chloride (QDM) (MW: 250,000) | 27.0 wt. % |
| Polyoxyethylene hydrogenated castor oil (E.O. 20) | 2.0 |
| Squalane | 0.5 |
| 1-Isostearoyl-3-myristoyl glycerol (DGMI) | 1.5 |
| 86% Glycerol | 2.0 |
| Propylene glycol | 1.0 |
| Sericite | 3.0 |
| Ethanol | 5.0 |
| Antiseptic | suitable amount |
| Water | balance |

Example 8

A keratotic plug remover having the following formulation was prepared.

| | |
|---|---|
| Polymethacryloyloxy trimethyl ammonium chloride (QDM) (MW: 200,000) | 15.0 wt. % |
| Polymethacrylamidepropyl trimethyl ammonium chloride (MAPTAC) (MW: 300,000) | 15.0 |
| Polyoxyethylene hydrogenated castor oil (E.O. 40) | 1.5 |
| Squalene | 0.5 |
| 2-Ethylhexanoic triglyceride | 2.0 |
| Sorbitol | 3.0 |
| Kaolin | 7.0 |
| Titanium oxide | 2.0 |
| Ethanol | 5.0 |
| Antiseptic | suitable amount |
| Water | balance |

What is claimed is:

1. A method for removing keratotic plugs from skin with a cosmetic article, which comprises:

wetting the skin or said cosmetic article;

applying onto the skin said cosmetic article; and peeling off said cosmetic article after drying;

wherein said cosmetic article comprises:

i) a substrate selected from the group consisting of woven cloth, non-woven cloth and a plastic film; and ii) on said substrate, a layer comprising a copolymer, in an amount effective to remove keratotic plugs, wherein said copolymer is a poly(alkyl vinyl ether/maleic acid) copolymer or a polyalkyvinyl ether/maleic anhydride) copolymer.

2. The method of claim 1, wherein said copolymer comprises methyl vinyl ether and maleic anhydride.

3. The method of claim 1, wherein said substrate is a non-woven cloth.

4. The method of claim 1, wherein said substrate is a woven or non-woven cloth selected from the group consisting of cotton, rayon, teton and nylon.

5. The method of claim 1, wherein said substrate is a non-woven rayon cloth.

6. The method of claim 1, wherein said layer comprises 5 to 70 wt. % based on the total weight of said layer of said copolymer.

7. The method of claim 1, wherein said layer comprises 5 to 40 wt. % based on the total weight of said layer of said copolymer.

* * * * *

UNITED STATES PATENT AND TRADEMARK OFFICE
CERTIFICATE OF CORRECTION

PATENT NO.    : 6,306,382 B1
DATED         : October 23, 2001
INVENTOR(S)   : Tomohiro Uemura et al.

Page 1 of 1

It is certified that error appears in the above-identified patent and that said Letters Patent is hereby corrected as shown below:

<u>Title page,</u>
Item [73], the Assignee information, should read:
-- [73] Assignees: Kao Corporation, Tokyo (JP);
          The Andrew Jergens Company, Cincinnati (OH) --

Item [60], should be deleted and replaced with Item [63].
Item [63], the Related U.S. Application Data should read:
--       Related U.S. Application Data
[63] Continuation of application No. 08/463,274, filed
    on Jun 5. 1995, now abandoned, which is a continuation
    of application No. 08/210,778, filed on Mar. 21, 1994,
    now Pat. No. 5,512,277, which is a contination of application
    No. 07/882,979, filed on May 14, 1992, now abandoned.

Signed and Sealed this

Fifteenth Day of January, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,306,382 B1                           Page 1 of 1
DATED         : October 23, 2001
INVENTOR(S)   : Tomohiro Uemura et al.

It is certified that error appears in the above-identified patent and that said Letters Patent is hereby corrected as shown below:

<u>Column 14,</u>
Line 3, "teton" should read -- tetron --.

Signed and Sealed this

Twenty-ninth Day of April, 2003

JAMES E. ROGAN
*Director of the United States Patent and Trademark Office*